(12) United States Patent
Zhang et al.

(10) Patent No.: US 12,303,722 B2
(45) Date of Patent: May 20, 2025

(54) ULTRASOUND SYSTEM, APPARATUS, AND METHOD FOR TRANSCRANIAL TREATMENT

(71) Applicants: Yi Zhang, Mineola, NY (US); Benjamin Zhang, New York, NY (US)

(72) Inventors: Yi Zhang, Mineola, NY (US); Benjamin Zhang, New York, NY (US)

(*) Notice: Subject to any disclaimer, the term of this patent is extended or adjusted under 35 U.S.C. 154(b) by 295 days.

(21) Appl. No.: 17/859,542

(22) Filed: Jul. 7, 2022

(65) Prior Publication Data

US 2023/0015807 A1    Jan. 19, 2023

Related U.S. Application Data

(60) Provisional application No. 63/218,982, filed on Jul. 7, 2021.

(51) Int. Cl.
| | | |
|---|---|---|
| *A61N 7/02* | (2006.01) | |
| *A61B 8/00* | (2006.01) | |
| *A61B 8/06* | (2006.01) | |
| *A61B 18/00* | (2006.01) | |

(52) U.S. Cl.
CPC ............ *A61N 7/02* (2013.01); *A61B 8/06* (2013.01); *A61B 8/4209* (2013.01); *A61B 8/54* (2013.01); *A61B 2018/00404* (2013.01); *A61B 2018/00434* (2013.01)

(58) Field of Classification Search
CPC .... A61N 7/02; A61N 7/00; A61N 2007/0021; A61N 2007/0078
See application file for complete search history.

(56) References Cited

U.S. PATENT DOCUMENTS 8,603,014 B2 * 12/2013 Alleman .............. A61B 8/4427
601/2

OTHER PUBLICATIONS

Rink C., et al., "Significance of Brain Tissue Oxygenation and the Arachidonic Acid Cascade in Stroke," Antioxidants & Redox Signaling, 2011, vol. 14, No. 10, pp. 1889-1903, Mary Ann Liebert, Inc.
Lauritzen M., "Pathophysiology of the migraine aura. The spreading depression theory," Brain, 1994, vol. 117, pp. 199-210, Oxford University Press.
Uemura M.T., et al., "Brain Microvascular Pericytes in Vascular Cognitive Impairment and Dementia," Frontiers in Aging Neuroscience, Apr. 2020, vol. 12, Article 80, pp. 1-22.
Johnson N.A., et al., "Pattern of Cerebral Hypoperfusion in Alzheimer Disease and Mild Cognitive Impairment Measured with Arterial Spin-labeling MR Imaging: Initial Experience," Radiology, Mar. 2005, vol. 234, No. 3, pp. 851-859, RSNA.

(Continued)

*Primary Examiner* — Peter Luong
(74) *Attorney, Agent, or Firm* — Carter, DeLuca & Farrell LLP

(57) ABSTRACT

The present disclosure relates to transcranial ultrasound systems, devices, and methods which are used for treatment rather than for imaging or medical diagnosis. In accordance with one aspect, a system for applying ultrasound energy includes at least three ultrasound applicators configured to be secured against a head of a person and configured to apply ultrasound energy to the head of the person when activated, and a controller configured to control activation and deactivation of the at least three ultrasound applicators based on a predetermined treatment sequence.

17 Claims, 2 Drawing Sheets

(56) References Cited

OTHER PUBLICATIONS

Wei W., et al., "Trajectories in Cerebral Blood Flow Following Antidepressant Treatment in Late-Life Depression: Support for the Vascular Depression Hypothesis," J Clin Psychiatry, 2019, vol. 79, No. 6, pp. 1-20.

Yang W.H., et al., "Regional cerebral blood flow in children with autism spectrum disorders: a quantitative 99mTc-ECD brain SPECT study with statistics parametric mapping evaluation," Chinese Medical Journal, 2011, vol. 124, No. 9, pp. 1362-1366.

Lee J.S., et al., "Regional Cerebral Blood Flow in Children With Attention Deficit Hyperactivity Disorder: Comparison Before and After Methylphenidate Treatment," Human Brain Mapping, 2005, vol. 24, pp. 157-164, Wiley-Liss, Inc.

Monti L., et al., "Impaired Cerebral Perfusion in Multiple Sclerosis: Relevance of Endothelial Factors," Biomarker Insights, 2018, vol. 13, pp. 1-10, Sage Publications.

Stewart J.M., et al., "Oscillatory Cerebral Blood Flow Is Associated With Impaired Neurocognition and Functional Hyperemia in Postural Tachycardia Syndrome During Graded Tilt," Hypertension, 2015, vol. 65, p. 636-443, American Heart Association, Inc.

Taguchi S., et al., "Motor Improvement-Related Regional Cerebral Blood Flow Changes in Parkinson's Disease in Response to Antiparkinsonian Drugs," Parkinson's Disease, 2019, vol. 2019, Article ID 7503230, pp. 1-8, Hindawi.

Derejko M., et al., "Regional cerebral blood flow in Parkinson's disease as an indicator of cognitive impairment," Nuclear Medicine Communications, 2006, vol. 27, No. 12, pp. 945-951, Lippincott Williams & Wilkins.

Speed C.A., "Therapeutic ultrasound in soft tissue lesions," Rheumatology, 2001, vol. 40, pp. 1331-1336, British Society for Rheumatology.

Tyler W.J., et al., "Remote Excitation of Neuronal Circuits Using Low-Intensity, Low-Frequency Ultrasound," PLoS One, 2008, vol. 3, Issue 10:e3511, pp. 1-11.

Barreto A.D., et al., "CLOTBUST-Hands Free Pilot Safety Study of a Novel Operator-Independent Ultrasound Device in Patients with Acute Ischemic Stroke," Stroke, 2013, vol. 44, pp. 3376-3381, American Heart Association, Inc.

\* cited by examiner

ULTRASOUND SYSTEM, APPARATUS, AND METHOD FOR TRANSCRANIAL TREATMENT

CROSS-REFERENCE TO RELATED APPLICATIONS

This application claims priority to and the benefit of the filing date of U.S. Provisional Application No. 63/218,982, filed on Jul. 7, 2021, which is hereby incorporated by reference herein in its entirety.

TECHNICAL FIELD

The present disclosure relates to ultrasound, and more particularly, to ultrasound which may be used for transcranial treatment.

BACKGROUND

Ultrasound technology applies high frequency sound waves for various imaging and diagnosis purposes. For example, sonogram used for imaging typically applies sound waves in the 3-8 MHz range. Such imaging systems are very safe and are widely used for fetal imaging during pregnancy. Another example of ultrasound technology is high-frequency doppler ultrasound, which may be used for diagnosing blood flow and may apply sound waves of 40 MHz or 50 MHz or sound waves as high as 200 MHz. Imaging and diagnostic applications using ultrasound technology are safe and effective and, therefore, are widely used.

SUMMARY

The present disclosure relates to ultrasound which may be used for transcranial treatment, such as enhancing cerebral blood flow, among other things. Aspects of the present disclosure relate to transcranial ultrasound systems, devices, and methods which are used for treatment rather than for imaging or medical diagnosis.

In accordance with aspects of the present disclosure, a system for applying ultrasound energy includes at least three ultrasound applicators configured to be secured against a head of a person and configured to apply ultrasound energy to the head of the person when activated, and a controller configured to control activation and deactivation of the at least three ultrasound applicators based on a predetermined treatment sequence.

In various embodiments of the system, the at least three ultrasound applicators are positioned to apply ultrasound energy to blood vessels within the head of the person when activated. In various embodiments of the system, the blood vessels include an interior carotid artery, an exterior carotid artery, and a basilar artery.

In various embodiments of the system, the predetermined treatment sequence includes activating at least three ultrasound applicators successively one at a time.

In various embodiments of the system, the at least three ultrasound applicators include: a left ICA applicator configured to be positioned to apply ultrasound energy to an interior carotid artery of the head of the person from a left side of the person, a BA applicator configured to be positioned to apply ultrasound energy to a basilar artery of the head of the person, a right ICA applicator configured to be positioned to apply ultrasound energy to the interior carotid artery of the head of the person from a right side of the person, a left ECA applicator configured to be positioned to apply ultrasound energy to an exterior carotid artery of the head of the person from the left side of the person, and a right ECA applicator configured to be positioned to apply ultrasound energy to the exterior carotid artery of the head of the person from the right side of the person.

In various embodiments of the system, the predetermined treatment sequence includes successively activating, in order: the left ICA applicator, the BA applicator, the right ICA applicator, the left ECA application, and the right ECA applicator.

In various embodiments of the system, the system includes an adjustable head piece where the at least three ultrasound applicators are attached to the adjustable head piece and where the adjustable head piece is configured to be adjusted to secure the at least three ultrasound applicators against the head of the person.

In various embodiments of the system, the system includes a source of ultrasound energy, where the at least three ultrasound applicators are coupled to the source of ultrasound energy.

In various embodiments of the system, the controller is configured to control the source of ultrasound energy.

In accordance with aspects of the present disclosure, a method for applying ultrasound energy includes: securing at least three ultrasound applicators against a head of a person, where the at least three ultrasound applicators are configured to apply ultrasound energy to the head of the person when activated, and controlling activation and deactivation of the at least three of ultrasound applicators based on a predetermined treatment sequence.

In various embodiments of the method, the method includes positioning the at least three ultrasound applicators to apply ultrasound energy to blood vessels within the head of the person when activated. In various embodiments of the method, the blood vessels include an interior carotid artery, an exterior carotid artery, and a basilar artery.

In various embodiments of the method, the predetermined treatment sequence includes activating at least three ultrasound applicators successively one at a time.

In various embodiments of the method, the at least three ultrasound applicators include: a left ICA applicator configured to be positioned to apply ultrasound energy to an interior carotid artery of the head of the person from a left side of the person, a BA applicator configured to be positioned to apply ultrasound energy to a basilar artery of the head of the person, a right ICA applicator configured to be positioned to apply ultrasound energy to the interior carotid artery of the head of the person from a right side of the person, a left ECA applicator configured to be positioned to apply ultrasound energy to an exterior carotid artery of the head of the person from the left side of the person, and a right ECA applicator configured to be positioned to apply ultrasound energy to the exterior carotid artery of the head of the person from the right side of the person.

In various embodiments of the method, the predetermined treatment sequence includes successively activating, in order: the left ICA applicator, the BA applicator, the right ICA applicator, the left ECA application, and the right ECA applicator.

In various embodiments of the method, the at least three ultrasound applicators are attached to an adjustable head piece, and the method includes adjusting the adjustable head piece to secure the at least three ultrasound applicators against the head of the person.

In various embodiments of the method, the at least three ultrasound applicators are coupled to a source of ultrasound energy. In various embodiments of the method, controlling the activation and deactivation of the at least three ultrasound applicators includes controlling the source of ultrasound energy.

In accordance with aspects of the present disclosure, an apparatus includes an adjustable head piece and at least three ultrasound applicators attached to the adjustable head piece. The adjustable head piece is adjustable to secure the at least three ultrasound applicators against a head of a person, and the at least three ultrasound applicators are configured to apply ultrasound energy to the head of the person when activated.

In various embodiments of the apparatus, the at least three ultrasound applicators include: a left ICA applicator configured to be positioned to apply ultrasound energy to an interior carotid artery of the head of the person from a left side of the person, a BA applicator configured to be positioned to apply ultrasound energy to a basilar artery of the head of the person, a right ICA applicator configured to be positioned to apply ultrasound energy to the interior carotid artery of the head of the person from a right side of the person, a left ECA applicator configured to be positioned to apply ultrasound energy to an exterior carotid artery of the head of the person from the left side of the person, and a right ECA applicator configured to be positioned to apply ultrasound energy to the exterior carotid artery of the head of the person from the right side of the person.

Further details and aspects of exemplary embodiments of the present disclosure are described in more detail below with reference to the appended figures.

BRIEF DESCRIPTION OF THE DRAWINGS

A better understanding of the features and advantages of the disclosed technology will be obtained by reference to the following detailed description that sets forth illustrative embodiments, in which the principles of the technology are utilized, and the accompanying drawings of which.

DETAILED DESCRIPTION

The present disclosure relates to ultrasound which may be used for transcranial treatment, such as enhancing cerebral blood flow, among other things. Aspects of the present disclosure relate to transcranial ultrasound systems, devices, and methods which are used for treatment rather than for imaging or medical diagnosis.

Figure 1:
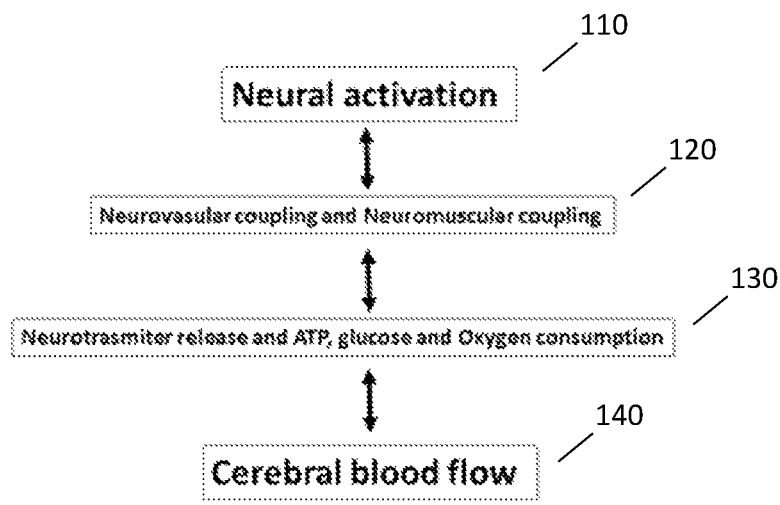
FIG. 1 is a block diagram of exemplary interactions within a brain, in accordance with aspects of the present disclosure.

Referring to FIG. 1, the brain is one of the most metabolically active organs in the body. Within the brain, oxygen consumption is highly dynamic and region specific. Oxygen transport from blood to tissue is driven by the oxygen concentration gradient between blood and tissue. The major oxygen concentration gradient has been found at the blood-tissue interface of arterioles. The oxygen, glucose and ATP production rate plays important roles in brain bioenergetics, function, and neuro-degeneration. Neuronal activity 110 is associated with increasing cerebral blood flow (CBF) 140.

Evidence suggests neurovascular coupling 120 is mediated through the free radical, nitric oxide (·NO) produced in neurons. Astrocytes also play a role in mediating CBF regulation during neuronal activation 110 by triggering Ca2+ release within astrocytic end feet and inducing various downstream Ca2+ signaling pathways to control vasodilation. Neuromuscular coupling 120 is most active in the perivascular region, in which there are ample opportunities for cell-cell interactions within the neurovascular unit (neurons, astrocytes, and parenchymal arterioles), and which maintains neurovascular function and cellular plasticity.

Hyperemia may be particularly important for preventing neuronal death in pathological conditions in which energy use is raised. When neurovascular/neuromuscular coupling 120 fails, CBF 140 decreases during the increased energy consumption 130, and central nervous system (CNS) disorders happen. For example:

Discontinuing CBF contribute in intracranial vessels causes Stroke or Transient Ischemic Attack. The intracranial stenosis, mild Traumatic Brain injury (TBI) or Vasospasm after sub-arachnoid hemorrhage causes decreasing CBF.

Migraine with aura suggests that the underlying mechanism is the cortical spreading depression. Studies show that cortical spreading depression in the neocortex is dependent on activation of NMDA receptor (one of the 3 subtypes of glutamate receptors). The NMDA receptor channels play an important role in synaptic plasticity and synapse formation underlying memory, learning and formation of neural networks during development in the CNS.

Prolonged CBF decreasing causes capillary pericytes constriction at the start of ischemia. Dysfunction of pericytes contribute Cerebral Small Vessel disease which lead to Vascular dementia. Pericytes loss causes BBB-breakdown, which stagnates amyloid beta clearance and leakage of neurotoxic molecules into the brain parenchyma which lead to Alzheimer's disease. Evidence shows Alzheimer's disease has regional cerebral hypoperfusion.

Regional CBF increases may be associated with decrease in Depression.

The decrease in CBF in Autism spectrum disorders has been studied.

Increasing CBF may be associated with improving Attention Deficit hyperactivity disorder (ADHD) to control attention and motor response to irrelevant environmental stimuli.

Studies show impaired cerebral perfusion in Multiple Sclerosis and the brain fog.

CBF decline may be associated with the cognitive impairment and motor impairment in Parkinson's disease.

Figure 2:
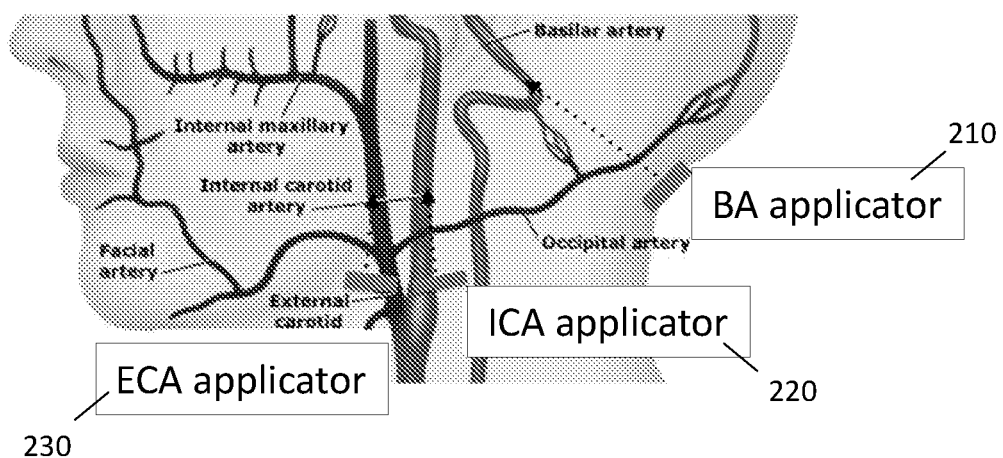
FIG. 2 is a diagram of blood circulation for the brain, in accordance with aspects of the present disclosure.

FIG. 2 shows a diagram of blood circulation for the brain. The brain receives blood from two sources: anterior and posterior circulations. The anterior circulation includes the internal carotid arteries (ICA) and external carotid artery (ECA), which arise in the neck where common carotid arteries are bifurcated. The posterior circulation includes the vertebral arteries which come together to form the basilar artery (BA). In stroke patients, ischemia can be improved by collateral circulation through the circle of Willis (internal) and anastomosis of ECA (external).

With continuing reference to FIG. 2, various ultrasound applicators 210-230 are positioned and operatively coupled to various areas of a person's head. The illustrated embodiment includes a BA applicator 210 which is positioned to direct ultrasound waves toward the basilar artery, an ICA applicator 220 which is positioned to direct ultrasound waves toward the internal carotid artery, and an ECA applicator 230 which is positioned to direct ultrasound waves toward the external carotid artery. As persons skilled in the art will understand, ultrasound refers to sound waves having frequencies above the human audible range, and ultrasound energy is a type of mechanical energy in the form of vibrating or moving particles within a medium. In various embodiments, the ultrasound applicators 210-230 of FIG. 2 may provide ultrasound waves in the range of 2 MHz to 18 MHz. In various embodiments, two or more applicators 210-230 may apply the same ultrasound frequency. In various embodiments, two or more applicators 210-230 may apply different ultrasound frequencies. The number of applicators and positioning of applicators in FIG. 2 are exemplary, and variations are contemplated to be within the scope of the present disclosure. In various embodiments, there may be fewer ultrasound applicators or a greater number of ultrasound applicators. In various embodiments, ultrasound applicators may be positioned to direct ultrasound energy to other blood vessels shown in FIG. 2 and/or to blood vessels not shown in FIG. 2. Such and other variations are contemplated to be within the scope of the present disclosure.

Figure 3:
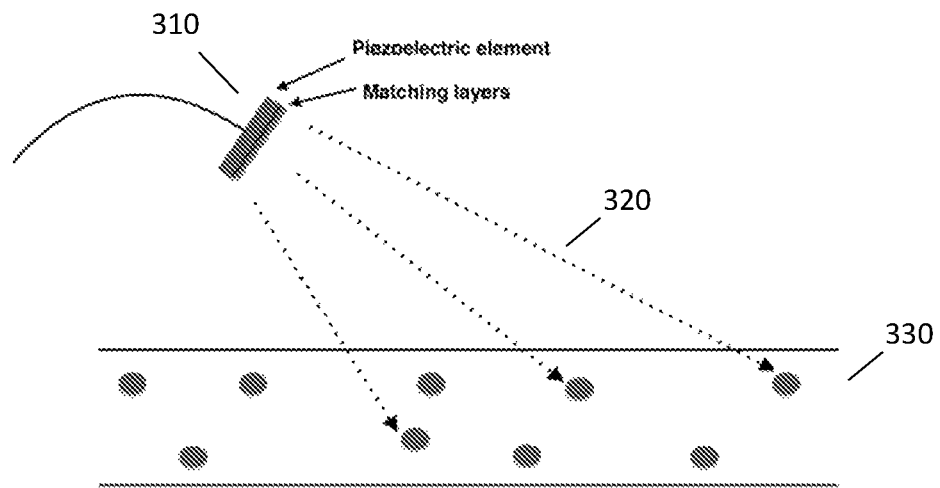
FIG. 3 is a diagram of an exemplary operation of an ultrasound applicator, in accordance with aspects of the present disclosure.
Figure 4:
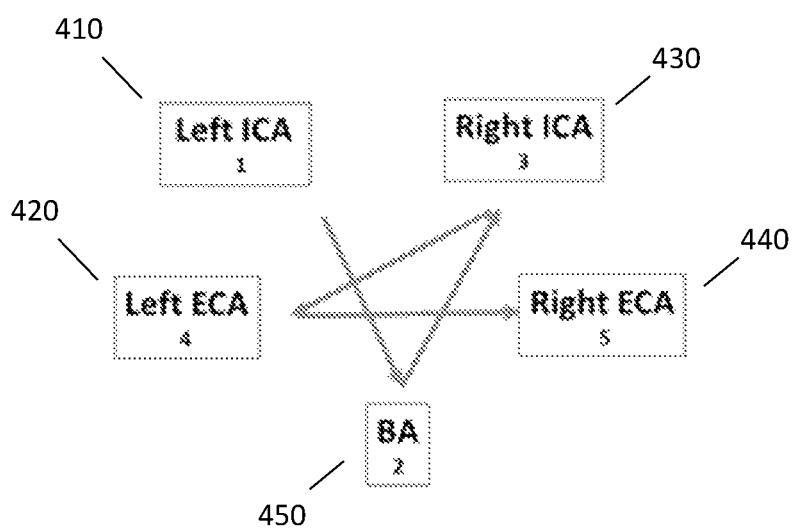
FIG. 4 is a flow diagram of an exemplary treatment operation, in accordance with aspects of the present disclosure.

Referring to FIG. 3, there is shown an operation of an ultrasound applicator 310, which may be any ultrasound applicator shown in FIG. 2 or FIG. 4. As mentioned above, ultrasound energy is a type of mechanical energy in the form of vibrating or moving particles within a medium. Ultrasound waves are provided by an ultrasound transducer, which may include a piezoelectric element and matching layers. The ultrasound waves 320 propagate through a medium (not shown) to reach its intended target, which may be blood vessels 330 in the head, in accordance with aspects of the present disclosure. The ultrasound waves 320 are attenuated as they propagate. The attenuation is partly due to conversion of mechanical wave energy into thermal energy.

In accordance with aspects of the present disclosure, the energy from ultrasound waves 320, including converted heat energy, can operate to dilate blood vessels 330 and/or increase oxygen presence in a target area. Additionally, the thermal effects of ultrasound waves 320 upon tissue can increase blood flow, reduce muscle spasm, and increase extensibility of collagen fibers and a pro-inflammatory response. Accordingly, ultrasound waves 320 directed to areas of the brain, in accordance with aspects of the present disclosure, can operate to provide a useful and effective way of non-invasively modulating brain circuit activity.

Referring now to FIG. 4, there is shown a diagram of an exemplary operation for applying ultrasound waves for intracranial treatment. In accordance with aspects of the present disclosure, the configuration of FIG. 4 includes five ultrasound applicators, including a left ICA applicator 410, a left ECA applicator 420, a right ICA applicator 430, a right ECA applicator 440, and a BA applicator 450. The left ICA applicator 410 is position at a left side a person's head to direct ultrasound energy toward the interior carotid artery. The right ICA applicator 430 is position at a right side a person's head to direct ultrasound energy toward the interior carotid artery. The left ECA applicator 420 is position at a left side a person's head to direct ultrasound energy toward the exterior carotid artery. The right ECA applicator 440 is position at a right side a person's head to direct ultrasound energy toward the exterior carotid artery. The BA applicator 450 is positioned to direct ultrasound energy toward the basilar artery.

In various embodiments, each applicator 410-450 may be thin so that the applicator can easily approach and be positioned at the occipital window and submandibular windows. In various embodiments, the applicators 410-450 may adhere to the head of a person using an adhesive. In various embodiments, the applicators 410-450 may be set within an adjustable head piece (not shown) (e.g., a helmet, etc.), which may be adjusted to bring each applicator in contact with the head of a person. Other manners of positioning and coupling ultrasound applications to a person's head are contemplated to be within the scope of the present disclosure. In various embodiments, the ultrasound applicators 410-450 can deliver 2 MHz pulses toward and into the blood stream of the interior carotid artery, the exterior carotid artery, and the basilar artery.

FIG. 4 also illustrates an exemplary sequence of activating and deactivating the applicators 410-450. As used herein, the term "activate" refers to and includes commencing delivery of ultrasound energy and/or continuing delivery of ultrasound energy, and the term "deactivate" refers to and includes ending delivery of ultrasound energy and/or continuing non-delivery of ultrasound energy. In the embodiment of FIG. 4, the sequence of activating the applicators 410-450 includes, in order: (1) left ICA applicator 410, (2) BA applicator 450, (3) right ICA applicator 430, (4) left ECA applicator 420, and (5) right ECA applicator 440. In an exemplary embodiment, all five ultrasound applicators 410-450 are initially set as off. At a first step, the left ICA applicator 410 is activated for five minutes. At a second step, the left ICA 410 applicator is deactivated and the BA applicator 450 is activated for five minutes. At a third step, the BA applicator is deactivated 450 and the right ICA applicator 430 is activated for five minutes. At a fourth step, the right ICA applicator 440 is deactivated and the left ECA applicator 420 is activated for five minutes. At a fifth step, the left ECA applicator 420 is deactivated and the right ECA applicator 440 is activated for five minutes. In such an embodiment, the total treatment time is twenty-five minutes.

Such a treatment sequence and configuration is exemplary, and variations are contemplated to be within the scope of the present disclosure. For example, in various embodiments, there may be a greater number of ultrasound applicators or there may be fewer ultrasound applicators. The applicators may be positioned to target other blood vessels, additional blood vessels, or fewer blood vessels. In various embodiments, the applicators are controlled such that only one applicator is activated at any moment. In various embodiments, one applicator may be activated while another applicator is being deactivated, such that there may be a time period when two or more applicators deliver some degree of ultrasound energy at the same time. In various embodiments, more than one applicator may be activated at the same time and/or more than one applicator may be deactivated at the same time. In various embodiments, the applicators may be activated for the same amount of time or for different amounts of time. For example, two or more applicators may be activated for the same amount of time, and/or two or more applicators may be activated for different amounts of time. Such and other variations are contemplated to be within the scope of the present disclosure.

Accordingly, described above are systems, apparatuses, and methods which can provide non-invasive neuromodulation using thermal and mechanical effects of ultrasound to enhance CBF to treat and/or prevent Stroke, Dementia, Depression, Migraine, Autism, TIA, ADHD, complications after mild TBI, MS, intracranial stenosis, brain fog, and/or Parkinson's disease, and which may enhance neuroplasticity, memory, concentration, and/or learning capabilities.

Aspects of the disclosed systems, apparatuses, and methods may utilize one or more controllers to control the ultrasound applicators. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods or operations may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

The following describes experiment results from applying the disclosed technology to ten people to stimulate cerebral blood flow in the interior carotid artery and the basilar artery. After applying the disclosed technology, changes of velocity of middle cerebral artery at the baseline velocity and the velocity after stimulated ICA and BA were recorded. This data is summarized in Table 1 below, in which "vMCA" refers to mean flow velocity of middle cerebral artery.

The data was analyzed by t-test. The two-tailed P value was 0.001. The 95% confidence interval of the difference was −7.20 (−10.64; −3.76). The experiment showed that applying ultrasound to stimulate blood flow in the interior carotid artery and the basilar artery can significantly increase cerebral blood flow and perfusion.

TABLE 1

|  | Age | Sex | vMCA Baseline (cm/sec) | vMCA after stimulation (cm/sce) | The change of vMCA |
|---|---|---|---|---|---|
| #1 | 48 | F | 65 | 70 | 5 |
| #2 | 18 | F | 44 | 51 | 7 |
| #3 | 72 | M | 37 | 49 | 12 |
| #4 | 85 | F | 58 | 66 | 8 |
| #5 | 83 | F | 69 | 73 | 4 |
| #6 | 22 | F | 62 | 61 | −1 |
| #7 | 47 | M | 80 | 92 | 12 |
| #8 | 48 | F | 80 | 95 | 15 |
| #9 | 72 | M | 45 | 52 | 7 |
| #10 | 78 | F | 60 | 63 | 3 |

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed:

1. A system for applying ultrasound energy, comprising:
   at least five ultrasound applicators configured to be secured against a head of a person and configured to apply ultrasound energy to the head of the person when activated, the at least five ultrasound applications comprising:
      a left ICA applicator configured to be positioned to apply ultrasound energy to an interior carotid artery of the head of the person from a left side of the person,
      a BA applicator configured to be positioned to apply ultrasound energy to a basilar artery of the head of the person,
      a right ICA applicator configured to be positioned to apply ultrasound energy to the interior carotid artery of the head of the person from a right side of the person,
      a left ECA applicator configured to be positioned to apply ultrasound energy to an exterior carotid artery of the head of the person from the left side of the person, and
      a right ECA applicator configured to be positioned to apply ultrasound energy to the exterior carotid artery of the head of the person from the right side of the person; and
   a controller configured to control activation and deactivation of the at least five ultrasound applicators based on a predetermined treatment sequence.

2. The system of claim 1, wherein the at least five ultrasound applicators are positioned to apply ultrasound energy to blood vessels within the head of the person when activated.

3. The system of claim 2, wherein the blood vessels include an interior carotid artery, an exterior carotid artery, and a basilar artery.

4. The system of claim 1, wherein the predetermined treatment sequence includes activating at least five ultrasound applicators successively one at a time.

5. The system of claim 4, wherein the predetermined treatment sequence includes successively activating, in order: the left ICA applicator, the BA applicator, the right ICA applicator, the left ECA application, and the right ECA applicator.

6. The system of claim 1, further comprising an adjustable head piece, wherein the at least five ultrasound applicators are attached to the adjustable head piece,
wherein the adjustable head piece is configured to be adjusted to secure the at least five ultrasound applicators against the head of the person.

7. The system of claim 1, further comprising a source of ultrasound energy, wherein the at least five ultrasound applicators are coupled to the source of ultrasound energy.

8. The system of claim 7, wherein the controller is configured to control the source of ultrasound energy.

9. A method for applying ultrasound energy, comprising:
securing at least five ultrasound applicators against a head of a person, the at least five ultrasound applicators configured to apply ultrasound energy to the head of the person when activated, wherein the at least five ultrasound applicators comprise:
a left ICA applicator configured to be positioned to apply ultrasound energy to an interior carotid artery of the head of the person from a left side of the person,
a BA applicator configured to be positioned to apply ultrasound energy to a basilar artery of the head of the person,
a right ICA applicator configured to be positioned to apply ultrasound energy to the interior carotid artery of the head of the person from a right side of the person,
a left ECA applicator configured to be positioned to apply ultrasound energy to an exterior carotid artery of the head of the person from the left side of the person, and
a right ECA applicator configured to be positioned to apply ultrasound energy to the exterior carotid artery of the head of the person from the right side of the person; and
controlling activation and deactivation of the at least five of ultrasound applicators based on a predetermined treatment sequence.

10. The method of claim 9, further comprising positioning the at least five ultrasound applicators to apply ultrasound energy to blood vessels within the head of the person when activated.

11. The method of claim 10, wherein the blood vessels include an interior carotid artery, an exterior carotid artery, and a basilar artery.

12. The method of claim 9, wherein the predetermined treatment sequence includes activating at least five ultrasound applicators successively one at a time.

13. The method of claim 12, wherein the predetermined treatment sequence includes successively activating, in order: the left ICA applicator, the BA applicator, the right ICA applicator, the left ECA application, and the right ECA applicator.

14. The method of claim 9, wherein the at least five ultrasound applicators are attached to an adjustable head piece,
the method further comprising adjusting the adjustable head piece to secure the at least five ultrasound applicators against the head of the person.

15. The method of claim 9, wherein the at least five ultrasound applicators are coupled to a source of ultrasound energy.

16. The method of claim 15, wherein controlling the activation and deactivation of the at least five ultrasound applicators includes controlling the source of ultrasound energy.

17. An apparatus comprising:
an adjustable head piece; and
at least five ultrasound applicators attached to the adjustable head piece, wherein the adjustable head piece is adjustable to secure the at least five ultrasound applicators against a head of a person,
wherein the at least five ultrasound applicators are configured to apply ultrasound energy to the head of the person when activated, and
wherein the at least three ultrasound applicators comprise:
a left ICA applicator configured to be positioned to apply ultrasound energy to an interior carotid artery of the head of the person from a left side of the person;
a BA applicator configured to be positioned to apply ultrasound energy to a basilar artery of the head of the person;
a right ICA applicator configured to be positioned to apply ultrasound energy to the interior carotid artery of the head of the person from a right side of the person;
a left ECA applicator configured to be positioned to apply ultrasound energy to an exterior carotid artery of the head of the person from the left side of the person; and
a right ECA applicator configured to be positioned to apply ultrasound energy to the exterior carotid artery of the head of the person from the right side of the person.

* * * * *